United States Patent [19]
Mavrovic

[11] 3,981,684
[45] *Sept. 21, 1976

[54] APPARATUS FOR CONTROLLING UREA SYSTEM

[76] Inventor: Ivo Mavrovic, 530 E. 72nd St., New York, N.Y. 10021

[ * ] Notice: The portion of the term of this patent subsequent to Feb. 24, 1993, has been disclaimed.

[22] Filed: Oct. 15, 1975

[21] Appl. No.: 622,531

Related U.S. Application Data

[60] Division of Ser. No. 468,255, May 9, 1974, Pat. No. 3,940,440, which is a continuation of Ser. No. 88,272, Nov. 10, 1970, abandoned.

[52] U.S. Cl. .............................. 23/260; 23/253 A; 137/93; 260/698; 260/700
[51] Int. Cl.² ...................... B01J 1/00; G05D 11/00
[58] Field of Search .............. 23/253 A, 230 A, 260; 260/555 A, 698, 700; 137/93

[56] References Cited
UNITED STATES PATENTS

| 3,124,148 | 3/1964 | Kleiss et al. | 137/93 |
| 3,146,263 | 8/1964 | Otsuka | 260/555 A |
| 3,531,521 | 9/1970 | Zen et al. | 260/555 A |

*Primary Examiner*—Joseph Scovronek
*Attorney, Agent, or Firm*—Flynn & Frishauf

[57] ABSTRACT

Internal water balance within a liquid carbamate recycle urea process is controlled. Pressure in decomposer and/or condenser system can be varied to effect control. Also, refractive index of carbamate recycle solution can be determined and related to water balance.

20 Claims, 2 Drawing Figures

APPARATUS FOR CONTROLLING UREA SYSTEM

RELATED APPLICATIONS

This application is a division of application Ser. No. 468,255, filed May 9, 1974, now U.S. Pat. No. 3,940,440, issued Feb. 24, 1976, which is a continuation of application Ser. No. 88,272, filed Nov. 10, 1970 (now abandoned).

FIELD OF INVENTION

This invention relates to a apparatus method for the continuous determination of the concentration of the carbamate recycle solution reactor feed stream within a urea synthesis process, and to a new apparatus for automatic control of the internal water balance within a liquid carbamate recycle urea synthesis process.

BACKGROUND OF THE INVENTION

Urea is commercially obtained by reacting $NH_3$ and $CO_2$ in a reactor at elevated temperature and pressure. At urea synthesis conditions $NH_3$ and $CO_2$ instantaneously and completely react stoichiometrically to form ammonium carbamate. The latter is partially converted to urea and water within 20–30 minutes of residence in the reactor. Ammonia in excess of the stoichiometric ratio with $CO_2$ is used in the reactor for the purpose of increasing the conversion of carbamate to urea. The urea synthesis reactor usually contains urea, water, excess ammonia and unconverted ammonium carbamate. For the purpose of separating the finished urea solution product from the unconverted reactants, the urea reactor effluent is usually let down in pressure through a reducing valve and heated in a decomposer, usually operated at a constant pressure, and thus the unconverted ammonium carbamate is decomposed to gaseous $NH_3$ and $CO_2$, and the gas is expelled from the urea product solution together with the excess ammonia evaporated from the latter with some water.

The $NH_3$ and the $CO_2$ gas with water vapor thus recovered is usually absorbed in water to form an aqueous ammoniacal solution of ammonium carbamate, and the solution thus obtained is recycled back to the urea synthesis reactor for total recovery.

The water contained in the recycle carbamate solution is detrimental to the conversion of ammonium carbamate to urea in the urea synthesis reactor. In order to minimize the adverse effect of the water upon the conversion of carbamate to urea in the reactor, the water content in the carbamate recycle solution is usually maintained at the lowest possible value. This minimum value is dependent upon the ammonium carbamate content of the carbamate recycle solution and consequently upon the salting-out temperature of carbamate. The water content in the carbamate recycle solution is usually maintained at such a level as to prevent the salting out of ammonium carbamate from the solution recycled to the reactor.

Thus, in practice, a continuous control of the water content in the carbamate recycle solution is required in order to prevent either the urea synthesis reactor from operating inefficiently, or to prevent crystallization of the carbamate recycle solution with obvious consequent mechanical problems in the equipment handling the carbamate recycle solution.

In practice such a continuous control of the water content in the carbamate recycle solution is difficult to achieve, because of the methods that are normally used to determine the water content in the carbamate recycle solution.

Analytical methods and various other methods are normally used to determine the concentration of the carbamate recycle solution.

One of the most commonly used methods is the analytical method, which mainly consists of taking a sample of the carbamate recycle solution and analyzing it in the laboratory for a complete determination of the ammonium carbamate expressed as equivalent $CO_2$, of the equivalent ammonia as ammonium carbamate and the free ammonia dissolved in water both expressed as total ammonia. The water content is obtained by difference, by substracting the determined values from the carbamate recycle solution.

The drawbacks of such an analytical method are obvious. Due to the usual minimum time lag of 6–7 hours between the time of the sampling of the carbamate recycle solution and the time the results of the laboratory analyses are available to the urea plant operator for the purpose of deciding how much water should be added to the carbamate recycle solution, or due to the several inherent possible sources of error in sampling and analysis of the carbamate recycle solution, efficient control cannot be realized.

Various other methods and techniques have been suggested in the past for a more or less continuous determination of the carbamate recycle solution concentration. These other methods consist mainly of monitoring one of the following four specific physical properties of the carbamate recycle solution: density, viscosity, electrical conductivity, or the specific velocity of sound through it.

These four basic methods based on the measurement of one of the specific physical properties of the carbamate recycle solution listed above, besides being subject to mechanical problems due to the delicate moving parts of the measuring apparatus in contact with the very corrosive carbamate recycle solution, have had the common problem of being relatively inaccurate and inconsistent due to a common cause. This common cause is due to the fact that each of the three components of the carbamate recycle solution, namely ammonium carbamate, free ammonia and water, has quite a different specific gravity, viscosity, electrical and sound conductivity. The difference between these four physical properties is relatively large especially for water and free ammonia. For example the specific gravity of water is one, and the specific gravity of liquid ammonia, when mixed with water, is about 0.71. The viscosity of water is equal to one centipoise, and that of liquid $NH_3$ is equal to about 0.16 centipoise. A similar relative difference exists between the other two physical properties of water and ammonia.

It is obvious that at the same ammonium carbamate to water ratio, the four physical properties of such a solution described above, namely specific gravity, viscosity, electrical and sound conductivity, are susceptible to the slightest variation in free $NH_3$ content of the carbamate recycle solution.

Due to the fact that the crystallization point of the carbamate recycle solution depends primarily upon the ratio of the dissolved ammonium carbamate to the water contained in the solution, and to a very minor degree depends upon the ratio of the dissolved free ammonia to the water contained in the solution, it is obvious that a relative variation in the crystallization point of the carbamate recycle solution can not be reliably detected by measuring one of the above mentioned four physical properties of the carbamate recycle solution.

In the above case, a relative variation in one of the above mentioned four physical properties of the carbamate recycle solution can be interpreted either as a variation in the crystallization point of the carbamate recycle solution due to a variation in the ratio of the dissolved ammonium carbamate to the water contained in the solution, or as a variation in the ratio of the dissolved free ammonia to the water contained in the solution without any consequent appreciable variation in the crystallization point of the carbamate recycle solution.

In a specific case wherein the physical property under observation, namely either the specific gravity, viscosity, electrical or the sound conductivity, remained relatively constant but at the same time the ammonium carbamate to water ratio and consequently the crystallization point of the carbamate recycle solution for instance increased by the same equivalent value of the particular physical property under observation, by which the free ammonia to water ratio decreased, it has been found that the crystallization point of the carbamate recycle solution and thus its concentration changed more or less drastically, but this relative change failed to be detected by observing the particular and above mentioned physical property under consideration, because the physical property under observation for the total carbamate recycle solution did not vary. In this case the relative increase in the value of the physical property under observation is counteracted by the equivalent decrease of the physical property under observation for the exactly same relative value, so that in effect no change of the physical property of the whole carbamate recycle solution is registered.

Various other methods of controlling the concentration of the carbamate recycle solution were suggested in the past, as for instance in the U.S. Pat. No. 3,270,050. A drawback of the process disclosed in U.S. Pat. No. 3,270,050 is the fact that the by-product biuret content in a urea product solution varies according to the temperature variations which occur in a degasser-evaporator.

Another drawback of the above mentioned process is the fact that the relationship between the concentration of a concentrated aqueous ammonium carbamate solution and its viscosity is not consistent.

SUMMARY OF THE INVENTION

The present invention provides a novel apparatus for controlling the internal water balance within a liquid carbamate recycle urea process. Contrary to common practice, the apparatus of the present invention comprises means for varying the pressure in one or in both low pressure decomposition-absorption systems for the purpose of controlling the amount of water evaporated from the aqueous urea solution product which is consequently recycled to the reactor.

Further, it has now been found that the concentration and the crystallization point of the carbamate recycle solution can be accurately and quickly determined by measuring its refractive index by means of a suitable refractive index measuring device.

The main reason for this is the fact that the values for the refractive index of water and liquid ammonia are relatively very close to each other, and that the value for the refractive index of ammonium carbamate differs quite markedly from those of liquid ammonia and water.

This novel apparatus for varying pressure to achieve the desired internal water balance control further enhances the synthesis process since the continuous indication of the relative refractive index of the carbamate recycle solution, obtained from a suitable refractive index measuring device, can be used to control the pressures to control the water balance.

SPECIFIC EMBODIMENTS OF THE INVENTION

By way of illustration, the refractive index of each of the components of a carbamate recycle solution is given below for reference:

|  | refractive index |
|---|---|
| liquid water | 1.3330 |
| liquid $NH_3$ | 1.3250 |
| solid ammonium carbamate | 1.54 (approx.). |

Another reason for this is the fact that by operating the vessel, in which the carbamate recycle solution is formed, at a fairly constant pressure and temperature, it has been found that the ratio of the free ammonia dissolved in the carbamate recycle solution to the water present in the carbamate recycle solution varies within a relatively narrow range for a relatively wide range of the ratio of the ammonium carbamate dissolved in the carbamate recycle solution to the water present in the carbamate recycle solution. This fact, plus the fact that the values for the refractive index of water and ammonia are relatively very close to each other and that the effect of a relatively small change in free ammonia to water ratio in the carbamate recycle solution has a negligible effect on the refractive index of the carbamate recycle solution due to the relatively great difference between the refractive index of ammonium carbamate and that of water and liquid ammonia, leads to the ultimate result that the concentration of ammonium carbamate in the carbamate recycle solution can be expressed as the ratio of the solute ammonium carbamate to the solvent aqua ammonia. To simplify matters, the ratio of $CO_2$ as ammonium carbamate can be related to the water present in the carbamate recycle solution. This ratio of $CO_2$ to water has been found to be proportional to the refractive index of the carbamate recycle solution and ultimately to the crystallization temperature of the carbamate recycle solution in a very wide range of the $CO_2$ to water weight ratio, for example from about 0.3 to about 4, and with a relatively great accuracy and consistency, for example with a maximum error in repeatability or deviation of about ±1°F. from an average carbamate crystallization curve determined on a carbamate recycle solution in the above mentioned $CO_2$ to water weight ratio from about 0.3 to about 4.

Thus, the continuous indication of the relative refractive index of the carbamate recycle solution, obtained from a suitable refractive index measuring device, can be transformed into a suitable continuous proportional signal, pneumatic, electrical etc., capable of operating a valve through which for instance the proper amount of water could be introduced into the vessel in which the carbamate recycle solution is formed for the purpose of constantly and automatically maintaining the $CO_2$ to water ratio in the carbamate recycle solution constant at a predetermined and preferred optimum value.

EXAMPLE 1

Figure 1:
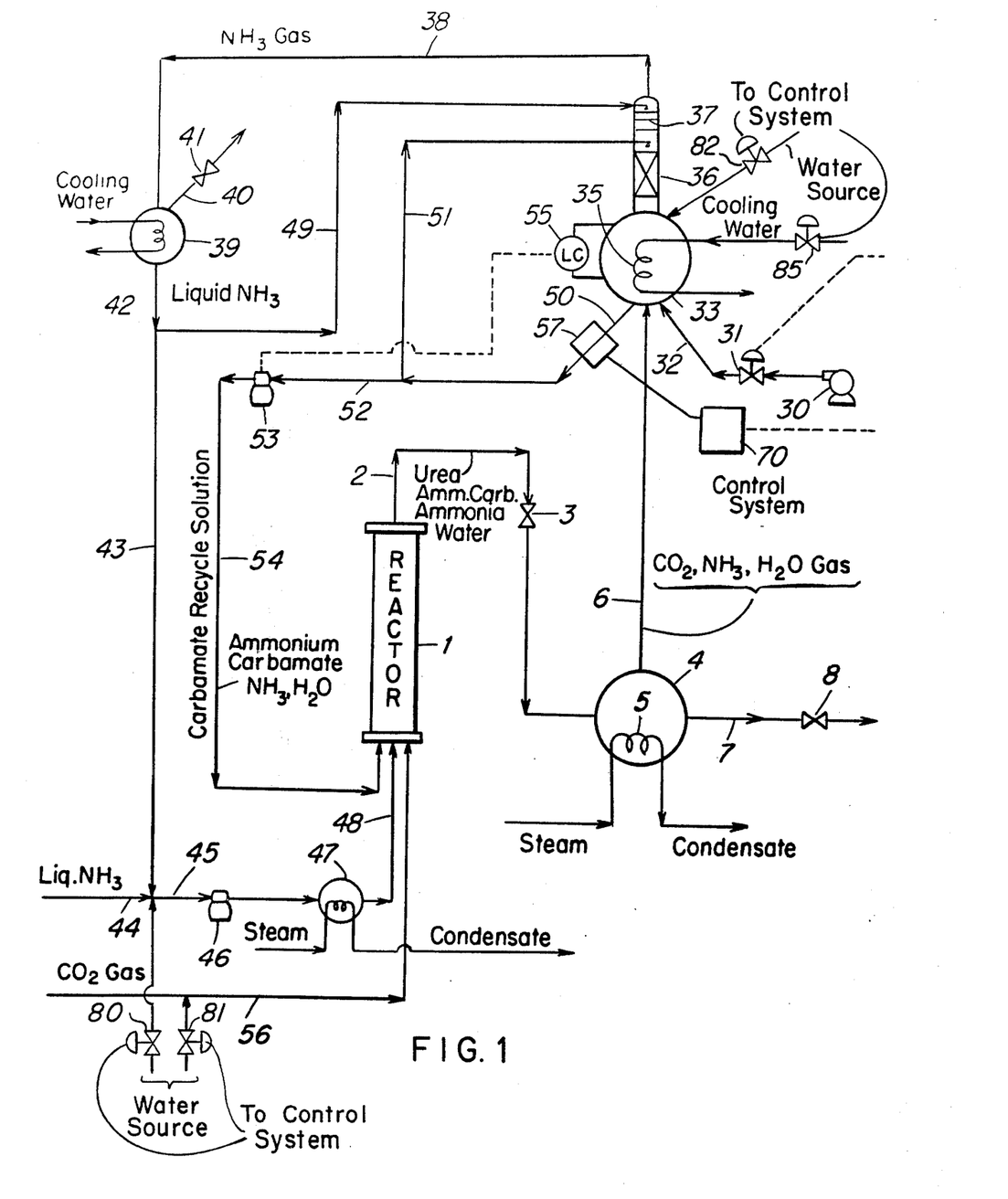
FIGS. 1 and 2, comprising two (2) sheets side-by-side, are a schematic block diagram of an urea synthesis system embodying the present invention.
Figure 2:
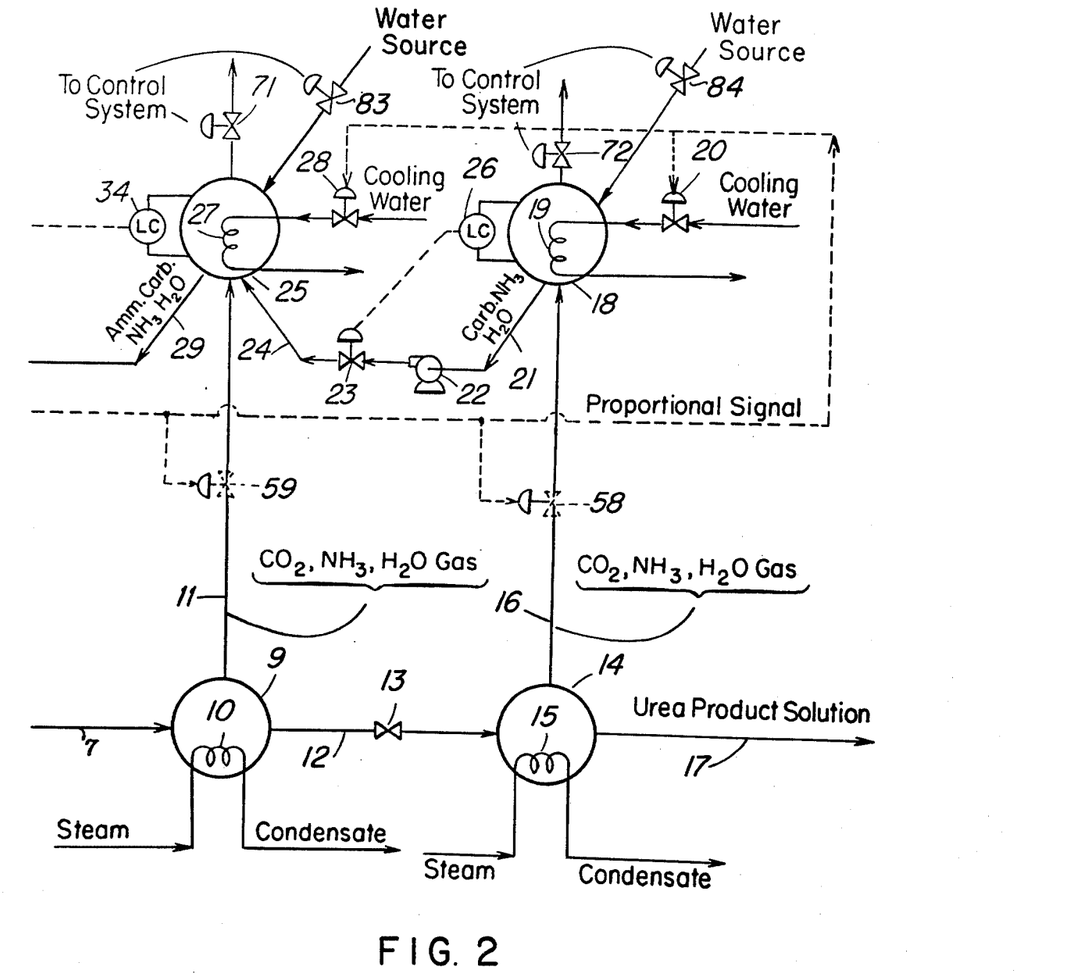

Referring to the Figures, a standard three stage decomposition and absorption liquid carbamate total recycle urea synthesis process is shown schematically. It is understood that a partial liquid carbamate recycle urea process wherein one or more of the gaseous streams from the decomposers and containing $NH_3$, $CO_2$ and water vapor are sent to an adjacent ammonium nitrate or sulfate plant for ammonia recovery, can be also operated in a similar manner to that one described in this example, as well as a system with a smaller or greater number of decomposition-absorption stages than described in this example.

Reactor 1 is operated in the pressure range from about 1500 psig to about 6000 psig and a temperature range from about 345° to about 420°F., in an overall $NH_3$ to $CO_2$ molar ratio of from about 2.2 to one to about 6 to one, in an overall $CO_2$ to water molar ratio of from about 0.1 to about 1.5, and in a conversion range of from about 40 to 80%, expressed as the percentage of $CO_2$ as urea formed in the reactor of the total amount of $CO_2$ as carbamate initially present in the reactor.

Reactor effluent stream 2 contains urea, water, unconverted ammonium carbamate and excess ammonia. The reactor effluent 2 is let down in pressure to about 300 psig through reducing valve 3 and is heated for the purpose of separating the aqueous product urea solution formed in the reactor from the residual unconverted ammonium carbamate and excess ammonia, present in the reactor effluent. In practice, this is done by heating the reactor effluent solution at a reduced pressure for the purpose of decomposing the unconverted ammonium carbamate to gaseous ammonia and $CO_2$ and of expelling the gas formed, from the aqueous urea product solution together with the excess ammonia evaporated from the aqueous urea product solution.

It is obvious that a certain amount of water vapor will be present in the $NH_3$—$CO_2$ gaseous phase issuing from a decomposer system, depending upon the operating conditions in the decomposition system. For convenience, three stages of decomposition and absorption are shown in the Figure, the stages being numbered respectively from one to three.

The first decomposer, 4, for example is shown to operate at about 300 psig and 310°F., the second decomposer, 9, at about 30 psig and 260°F., and the third decomposer, 14, at about 8 psig and 250°F.

As mentioned above, the reactor effluent stream 2 is reduced in pressure to about 300 psig through the reducing valve 3 and is introduced in the first decomposer 4. Steam is supplied to heating coil 5 to maintain the temperature of the product in the first decomposer 4 at about 310°F. The $NH_3$ and $CO_2$ gas thus formed in the first decomposer 4, containing some water vapor, is discharged from the first decomposer 4 through line 6.

An aqueous urea product solution stream 7 containing some residual ammonium carbamate and excess ammonia is discharged from the first decomposer 4, reduced in pressure to about 30 psig through pressure reducing valve 8 and is introduced into second decomposer 9. Steam is supplied to heating coil 10 to maintain the temperature of the product solution in the second decomposer 9 at about 260°F. The $NH_3$ and $CO_2$ gas thus formed in the second decomposer 9, containing some water vapor, is discharged therefrom through line 11.

An aqueous urea product solution stream 12 containing some residual ammonium carbamate and excess ammonia is discharged from the second decomposer 9, reduced in pressure to about 8 psig through pressure reducing valve 13 and is introduced into third decomposer 14.

Steam is supplied to heating coil 15 to maintain the temperature of the product solution in the third decomposer 14 at about 250°F. The $NH_3$ and $CO_2$ gas thus formed in the third decomposer 14 containing some water vapor, is discharged from the third decomposer 14 through line 16.

Aqueous urea product solution stream 17 essentially containing the urea and the water formed from ammonium carbamate in reactor 1 is discharged from the third decomposer 14 and further processed to its solid form or as required, in equipment not shown.

The gaseous stream 16 containing $NH_3$, $CO_2$ and water is condensed to solution in the third condenser 18 at about 130°F. and about 8 psig by removing the heat of condensation and reaction with cooling water circulated through cooling coil 19, provided with control valve 20. The pressure in the third condenser 18 is controlled by varying the operating temperature and thus the vapor pressure of the solution formed in the third condenser 18 by condensation of the gaseous stream 16. This variation in temperature of the solution formed in the condenser 18 is in turn attained by varying the flow of cooling water through cooling coil 19 by means of the control valve 20.

Thus, by varying the pressure in the third condenser 18, the pressure in the third decomposer 14 will also vary, so that the amount of water evaporated from the aqueous urea product solution 17 will vary and consequently the water vapor content of stream 16 leaving the third decomposer 14 will also vary.

The pressure in the third decomposer 14 can be directly controlled by means of a valve 58 located in line 16 from the third decomposer 14. In this case the pressure in the third condenser 18 can be maintained constant at a lower level than that in third decomposer 14, at the expense of some loss in efficiency in condenser 18.

In condenser 18, the water vapor is condensed to liquid water, part of the total $NH_3$ present in the gaseous stream 16 reacts with $CO_2$ to form ammonium carbamate which dissolves in the liquid water, and the remaining part of the total $NH_3$ present in the gaseous stream 16 dissolves in the liquid water. The aqueous ammoniacal solution of ammonium carbamate thus formed is discharged from the third condenser 18 through line 21, is elevated in pressure to about 30 psig by passage through pump 22 and is introduced through control valve 23 and line 24 into second condenser 25.

Automatic level controller 26, provided on the third condenser 18, maintains the level of liquid formed in the third condenser 18 at a constant height by regulating the opening of the level control valve 23, through which the solution formed in the third condenser 18 is passed into the second condenser 25.

Under normal operating conditions the amount of water vapor usually contained in the gaseous stream 16 and condensed to liquid water in the third condenser 18 is sufficient to maintain the carbamate formed in solution and to prevent it from crystallizing in the third condenser 18.

The second condenser 25 operates quite analogously to the third condenser 18 just described.

The gaseous stream 11 from the second decomposer 9 and containing $NH_3$, $CO_2$ and water vapor is introduced into the second condenser 25 together with the stream in line 24 withdrawn from the preceding third condenser 18. The gaseous stream 11 is condensed, reacted and dissolved to solution in the second condenser 25 operating at about 130°F. and at about 30 psig by removing heat from condenser 25 by means of cooling water circulated through the cooling coil 27, provided with control valve 28.

The pressure in the second condenser 25 is controlled by varying the operating temperature and thus the vapor pressure of the solution formed in the second condenser 25 by condensation of the gaseous stream 11 and by mixing it with the solution from line 24.

The variation in temperature of the solution formed in the condenser 25 is in turn attained by varying the flow of cooling water through cooling coil 27 by means of the control valve 28.

Analogously to the operation of the third decomposer 14 described above, by varying the pressure in the second condenser 25, the pressure in the second decomposer 9 also varies, so that the amount of water evaporated from the aqueous urea product solution in line 12 will also vary and consequently the water vapor content of stream 11 leaving the second decomposer 9 will also vary.

The pressure in the second decomposer 9 can be directly controlled by means of valve 59 located in line 11 from the second decomposer 9. In this case the pressure in the second condenser 25 can be maintained constant at a lower level than that in the second decomposer 9, at the expense of some loss in efficiency in the second condenser 25.

The water vapor contained in gaseous stream 11 is condensed to liquid, a part of the total $NH_3$ present in the gaseous stream 11 reacts with $CO_2$ to form ammonium carbamate which dissolves in the liquid water, and the remaining part of the total $NH_3$ present in the gaseous stream 11 dissolves in the liquid phase. The total amount of aqueous ammoniacal solution of ammonium carbamate thus formed by condensation of the gaseous stream 11 and by mixing the resulting solution with the liquid introduced into the second condenser 25 through line 24, is discharged from the second condenser 25 through line 29, elevated in pressure to about 300 psig by means of the pump 30 and is introduced through level control valve 31 and through line 32 into first condenser 33.

Automatic level controller 34 provided on the second condenser 25 maintains the level of liquid formed in the second condenser 25 at a constant height by regulating the opening of the level control valve 31, through which the solution formed in the second condenser 25 is passed into the first condenser 33.

The gaseous stream 6 from the first decomposer 4 and containing $NH_3$, $CO_2$ and water vapor is introduced into the first condenser 33 together with the liquid stream in line 32 withdrawn from the preceding second condenser 25. The gaseous stream 6 is partially condensed, reacted and dissolved to solution in the first condenser 33 operating at about 200°F. and about 300 psig by removing a predetermined amount of heat from condenser 33 by means of cooling water circulated through cooling coil 35.

The water vapor contained in the gaseous stream 6 is condensed to liquid and mixed with the solution introduced into the first condenser through line 32, a part of the total $NH_3$ present in the gaseous stream 6 reacts with $CO_2$ to form ammonium carbamate which dissolves in the solution present in the first condenser 33, and the remaining part of the total $NH_3$ of stream 6 which remains unabsorbed is cleaned from the residual $CO_2$ in packed section 36 and in the tray section 37 of condenser 33 and is passed through line 38 to water cooled $NH_3$ condenser 39.

The pressure in the ammonia condenser 39, in the first condenser 33 and in the first decomposer 4 is maintained at about 300 psig by venting inerts through line 40 and through control valve 41 on the ammonia condenser 39.

The liquid $NH_3$ condensed in condenser 39 is withdrawn from condenser 39 through line 42, and is split into two streams; the major part of the liquid $NH_3$ from stream 42 is passed through line 43, mixed with the fresh make up liquid $NH_3$ in line 44, is passed through line 45, elevated in pressure to about 3200 psig through pump 46, steam heated in liquid $NH_3$ preheater 47, and is introduced into the reactor 1 through line 48.

The minor part of stream 42 is passed through line 49 and introduced onto the top of the tray section 37 for the purpose of cleaning the stream of the uprising gaseous $NH_3$ from the last traces of of $CO_2$.

The ammoniacal aqueous solution of ammonium carbamate formed in the first condenser 33 is withdrawn from condenser 33 through line 50 and recirculated through line 51 over the packed section 36 for the purpose of counter-currently contacting the uprising stream of gaseous $NH_3$ and for scrubbing from it the major part of $CO_2$.

The level of liquid in the first condenser 33 is maintained constant by withdrawing an appropriate amount of the ammoniacal aqueous solution of ammmonium carbamate from line 50 through line 52, boosting it in pressure to about 3200 psig through carbamate plunger pump 53 and introducing it into the reactor 1 through line 54.

Automatic level controller 55 on the first condenser 33 maintains the liquid level constant in condenser 33 by regulating the speed of the reciprocating carbamate plunger pump 53 and thus its through-put of liquid.

Gaseous $CO_2$ at about 3200 psig is introduced into the reactor 1 through line 56.

The concentration of the ammoniacal aqueous solution of ammonium carbamate recycled to the reactor through line 54, or more exactly the ratio of $CO_2$ as carbamate to the water contained in the carbamate recycle solution of line 54, will depend upon the amount of water vapor contained in the gaseous streams 6, 11 and 16 evaporated from the urea product solution in the first decomposer 4, in the second decomposer 9 and in the third decomposer 14, respectively. The total amount of ammonium carbamate contained in the carbamate recycle stream 54 will depend upon the overall conversion of carbamate to urea in the reactor 1 and thus upon the amount of unconverted carbamate contained in the reactor effluent stream 2.

If the conversion in the reactor 1 increases, relatively less unconverted ammonium carbamate will be present in the reactor effluent stream 2 and consequently in the carbamate recycle stream 54. In this case, in order to maintain the ratio of $CO_2$ to water in stream 54 constant, it will be necessary to decrease the amount of water vapor evaporated from the aqueous urea product solution in the first decomposer 4, in the second decomposer 9 and in the third decomposer 14, respectively. In order to attain this, it is sufficient in practice to control the amount of water evaporated in one or both of decomposers 9 and 14. The water balance control in this case is accomplished by increasing the pressure in the decomposers 9 and 14, which, in turn, is accomplished by decreasing the flow of cooling water through the respective cooling water control valves 28 and 20, and cooling coils 27 and 19 as described above.

On the contrary, if the conversion in the reactor 1 decreases it will be necessary to increase the flow of cooling water through one or both control valves 28 and 20 in order to decrease the pressure in the second decomposer 9 and in the third decomposer 14, respectively, and thus to increase the amount of water evaporated in decomposers 9 and 14 and to increase the water content in streams 11 and 16, respectively.

Any variation in the rate of formation of the liquid phase formed in condensers 25 and 18 will be immediately sensed by the respective liquid level controllers 34 and 26, which, in turn, will proportionately reset the respective control valves 31 and 23 and vary the flow of solution through lines 32 and 24, respectively.

As an ultimate result, the ratio of $CO_2$ to water in the carbamate recycle solution 54 will be maintained constant at a predetermined and desired value, so as to prevent crystallization of the solution in lines 50, 51, 52 and 54, as shown below in the illustrative examples.

The line 50 from the first condenser 33 is provided with refractometric device 57 for the continuous determination of the refractive index of the carbamate recycle solution, according to the principles described before, so that the slightest relative variation in the $CO_2$ to water ratio in the carbamate recycle solution of stream 54 (and thus of streams 50, 51 and 52) will be detected by the refractometer 57 in the form of a relative proportional variation of the refractive index of the carbamate recycle solution of stream 50. This proportional variation of the refractive index is transformed into a suitable proportional signal, as described hereinbelow, capable of proportionally actuating either one or both control valves 28 and 20 on the cooling coils 27 and 19, respectively, and/or one or both valves 58 and 59.

By the method described above, refractometer 57 indirectly maintains the ratio of $CO_2$ to water in the carbamate recycle solution 54 constant by simply controlling one or both control valves 28 and 20, and/or one or both valves 58 and 59.

Refractometric device 57 can also be located in lines 51, 52 or 54, rather than in line 50. However, the location on line 50 as illustrated is preferred.

Refractometric device 57 can be an Anacon Refractometer, an Abbe Refractometer, a refractometer marketed by Electron Machine Company or any other similar device for determining a refractive index of a fluid.

Preferably refractometric device 57 is coupled to a conventional control system 70 which converts the refractive index measurements into pneumatic signals. Such a control system 70 is exemplified, for example, by conventional transducers and pneumatic controllers manufactured by Foxboro Instrument Corp. It should be clear that control system 70 is shown in the drawing as a single element merely by way of example. Valves 20, 28, 58 and 59 are preferably pneumatic valves when Foxboro transducers and controllers described above are used. Suitable valves are manufactured by the Fisher and Porter Co. The operation of such valves and their associated controls should be apparent to those skilled in the art. The level controllers shown in the drawing are also conventional. Suitable level controllers are manufactured by Taylor Instrument Co. and by Foxboro Instrument Corp. The speed of pump 53 is typically controlled by a conventional controller manufactured by Foxboro Instrument Corp.

The valves 20, 28, 58 and 59 may be operated in various combinations, or singly, to provide control of the urea synthesis process. The simplest and most efficient control, however, is achieved by operating only either or both of valves 20 and 28 to control pressures in response to refractive index variations.

Alternatively, or in conjunction with the operation of any or all of valves 20, 28, 58 and 59, control valves 71 and 72, which are pressure vent valves, may be operated to control the pressures in condensers 18 and 25. However, this is a less efficient manner to control system pressures. Control of pressure in condensers 18 and 25 via vent valves 71 and 72, respectively, also indirectly controls pressure in decomposers 9 and 14 by virtue of the interconnections therebetween.

Another case is possible, in which the conversion in the reactor does not vary, but the amount of water in the urea product solution 17 varies for some reason, for example due to a sudden slight variation in temperature in one or all decomposers 4, 9 and 14, respectively.

The urea product solution 17 normally contains about one mole of water per mole of urea formed in reactor 1. As mentioned above, if for example the temperature in one or in all the three decomposers 4, 9 and 14 suddenly increases, more water vapor will be evaporated from the aqueous urea solution and consequently the aqueous urea product solution stream 17 will contain less than one mole of water per mole of urea formed in reactor 1. In this case, the corresponding slight excess of water vapor present in either gaseous line 6, 11 and 16 will condense in its respective condensers 33, 25 and 18 and eventually accumulate in the first condenser 33. The consequence of this gradual accumulation of water in condenser 33 will result in a gradual dilution of the carbamate recycle stream 54 and thus in a gradual decrease in the ratio of $CO_2$ as carbamate to the water contained in the carbamate recycle stream 54. This gradual decrease in the $CO_2$ to water ratio will result in a gradual decrease in the refractive index of the carbamate recycle solution 54, which will be registered by the refractometer 57 connected to line 50. The decrease in refractive index sensed by refractometer 57 is transformed into a proportional signal, e.g. pneumatic or electrical, which, in turn, is utilized to increase the pressure in one or both decomposers 9 and 14 either by decreasing the flow of cooling water through the respective cooling coils 27 and 19 by means of the respective control valves 28 and 20 or by proportionately pinching the valves 59 and 58 on the respective gas lines 11 and 16. By increasing the pressure in one or both decomposers 9 and 14, less water will be evaporated from the aqueous urea product solution and thus present in the respective gaseous streams 11 and 16, with the ultimate result that the accumulation of water in the first condenser 33 and thus in the carbamate recycle solution 54 will be arrested and the original pre-fixed $CO_2$ to water ratio in stream 54 restored.

Completely the opposite of what is described above occurs if, for example, the temperature in one or both decomposers 9 and 14 suddenly decreases.

Still another case is possible, wherein water or water vapor is suddenly introduced in the process system of the Figure from an external source either in one of the make up streams 44 and 56, respectively containing $NH_3$ and $CO_2$ via respective valves 80, 81, or by directly feeding water to one or more of the condensers 33, 25 and 18 via respective valves 82, 83, 84. Again similarly to what is described above, in this case the sudden drop in the $CO_2$ to water ratio of stream 54 and thus in its refractive index will result in an automatic increase in pressure either in one or both decomposers 9 and 14, in a temporary increase in the water content of the aqueous urea product solution 17 and ultimately it will result in the restoring of the $CO_2$ to water ratio in stream 54 to its original and prefixed value.

Still another case is possible, wherein urea in its usual form of a more or less concentrated aqueous solution is continuously introduced from an external source into the process system of the Figures in a substantially constant stream, for example via the third condenser 18. At the first approach one would be inclined to assume that the presence of urea as a fourth component in the carbamate recycle solution 54 would cause the relation between the $CO_2$-water ratio in stream 54 and its refractive index to lose its consistency. In practice it is not so, because the stream of urea recycle introduced into the urea synthesis process system of the Figures is usually maintained constant. Such a urea stream is usually recycled to the urea synthesis process system from a urea solution handling and finishing unit not shown in the Figure, which can be either a urea crystallization, or a urea evaporation or a urea prilling section. Due to the fact that this stream of urea recycled to the urea synthesis process system is usually maintained rather constant, it is found that the ratio of the recycled urea to the water contained in the carbamate recycle stream 54 is also constant, and it is found again that a relative change in the refractive index of the total carbamate recycle solution stream 54 is essentially proportional to the $CO_2$ to water ratio in the carbamate recycle solution stream 54.

As an ultimate conclusion, it is found that the refractive index of the carbamate recycle solution 54 is proportional to the $CO_2$ water ratio of stream 54 regardless of the fact whether or not recycled urea is present in stream 54.

When urea is so present, it is in an amount of from about 0.005 to about 4 pounds of urea per pound of ammonium carbamate present in said liquid phase (ammonium carbamate solution) recycled to reactor 1.

It is to be understood that the material in line 51 is considered to be part of the liquid phase recycled to reactor 1.

EXAMPLE 2

Referring to the Figure, the reactor effluent stream in line 2 contains 25,000 lbs/hr of urea, 18,260 lbs/hr of unconverted ammonium carbamate, 18,540 lbs/hr of excess ammonia and 15,799 lbs/hr of water. Reactor 1 operates at about 375°F. and about 3200 psig.

The reactor effluent in line 2 is reduced in pressure to about 300 psig through the reducing valve 3 and is steam heated in the first decomposer 4 at about 310°F. and to about 300 psig.

The gaseous phase formed in decomposer 4 is passed through line 6. It contains 9400 lbs/hr of $CO_2$, 24,000 lbs/hr of $NH_3$ and, 4,860 lbs/hr of water vapor.

The remaining liquid phase separated in decomposer 4 is withdrawn through line 7. It contains 25,000 lbs/hr of urea, 1595 lbs/hr of residual carbamate, 1805 lbs/hr of residual free ammonia and 10,939 lbs/hr of water.

Stream 7 is let down in pressure to about 30 psig through the reducing valve 8 and is steam heated in the second decomposer 9 to about 260°F.

The gaseous phase formed in decomposer 9 is passed through line 11. It contains 450 lbs/hr of $CO_2$, 1300 lbs/hr of $NH_3$ and 1700 lbs/hr of water vapor.

The remaining liquid phase separated in decomposer 9 is withdrawn through line 12. It contains 25,00 lbs/hr of urea, 354 lbs/hr of residual ammonium carbamate, 246 lbs/hr residual free ammonia and 8239 lbs/hr of water.

Stream 12 is reduced in pressure to about 8 psig through the reducing valve 13 and heated in the third decomposer 14 to about 250°F.

The gaseous phase formed in decomposer 14 is passed through line 16. It contains 150 lbs/hr $CO_2$, 330 lbs/hr $NH_3$ and 740 lbs/hr of water vapor.

The liquid phase separated in decomposer 14 is withdrawn through line 17. It contains 25,000 lbs/hr of urea, 89 lbs/hr of residual carbamate, 31 lbs/hr of residual free ammonia and 7,499 lbs/hr of water.

The liquid stream 17 is the final aqueous urea product solution, which at the point of equilibrium of this urea synthesis process system with respect to the water balance contains one mole of water per mole of urea formed in reactor 1.

If water from an external source is added into the urea synthesis process system, at water balance equilibrium such amount of water will be discharged from the process system through line 17 in addition to the stoichiometric amount of 7,499 lbs/hr of water formed in reactor 1.

The gaseous stream from line 16 is condensed in the third condenser 18 at about 130°F. and about 8 psig. The heat of reaction is removed by circulating cooling water through cooling coil 19. The pressure in the third condenser 18, and thus in decomposer 14, is regulated by controlling the operating temperature of the solution in condenser 18 by means of valve 20 on the cooling water supply line to cooling coil 19.

The pressure in condenser 18 can be also controlled by venting a certain amount of gas from condenser 18, for example, by valve 72 as discussed hereinabove, but this method is somewhat uneconomical either because of the valuable $NH_3$ and $CO_2$ gas lost into the atmosphere or for the additional expenditure incurred in providing a suitable $NH_3$ and $CO_2$ recovery system for the vented gas.

The liquid formed in the third condenser 18 and containing 266 lbs/hr of ammonium carbamate, 214 lbs/hr of free ammonia and 740 lbs/hr of water is withdrawn from condenser 18 through line 21, boosted in pressure to about 30 psig through pump 22 and introduced into the second condenser 25 through line 24.

The level controller 26 maintains a constant liquid level in condenser 18 by actuating control valve 23, so that the total amount of liquid formed in condenser 18 is continuously passed to the second condenser 25 at the rate at which it is formed.

The gaseous stream from line 11, issuing from the second decomposer 9, is condensed in the second condenser 25 at about 130°F. and about 30 psig.

Completely analogously to the third condenser 18, the heat of reaction in condenser 25 is removed by cooling water in coil 27 and the pressure in condenser 25 is controlled by means of valve 28 on the cooling water supply line to cooling coil 27. In a less economical manner, pressure is controlled by venting valve 71.

The liquid formed in the second condenser 25 and containing 1506 lbs/hr of ammonium carbamate, 1774 lbs/hr of free ammonia and 3440 lbs/hr of water is withdrawn from condenser 25 through line 29, boosted in pressure to about 300 psig through pump 30 and introduced into the first condenser 33 through line 32.

The level controller 34 maintains a constant liquid level in condenser 25 by actuating control valve 31, so that the total amount of liquid formed in condenser 25 is continuously passed to the first condenser 33 at the rate at which it is formed.

The gaseous stream 6, issuing from the first decomposer 4, is partially condensed in the first condenser 33 at about 200°F. and at about 300 psig. The heat of reaction is removed by cooling water in coil 35 controlled by valve 85.

Part of the excess ammonia contained in stream 6 can not be dissolved in the solution formed in condenser 33, so that it is necessary to clean this part of unabsorbed excess free ammonia from the residual $CO_2$ in the packed column 36, over which part of the solution formed in condenser 33 is circulated through lines 50 and 51 for better contacting and scrubbing of the excess gaseous ammonia. The last traces of $CO_2$ are removed from the excess gaseous $NH_3$ in the tray section 37. About 10,000 lbs/hr of reflux liquid, $NH_3$ is fed to the top tray of tray section 37 through line 49 for the purpose of scrubbing $CO_2$ from the excess gaseous ammonia and for the purpose of removing the heat of reaction from the tray section 37 and from the packed section 36 by evaporation.

A mixture of 13,730 lbs/hr of process excess gaseous ammonia and about 10,000 lbs/hr of reflux gaseous ammonia is withdrawn from the top of the tray section 37 through line 38 at about 130°F. and condensed to liquid ammonia in the water cooled condenser 39 at about 95°F. The pressure in condenser 39 is maintained constant at about 300 psig by venting a controlled amount of inerts through line 40 and control valve 41. These inerts comprise the amount of $H_2$, $N_2$ and $CH_4$ usually present as impurities in the liquid ammonia make up stream 44 and in the gaseous $CO_2$ make up stream 56, respectively.

About 23,730 lbs/hr of liquid $NH_3$ is withdrawn from condenser 39 through line 42. About 10,000 lbs/hr of this amount is fed to the top of the tray section 37 through line 49, and 13,730 lbs/hr of liquid $NH_3$ is passed through line 43 and mixed with 14,236 lbs/hr of make up liquid ammonia from line 44. The mixture of the two streams in line 45, amounting to 27,966 lbs/hr of liquid $NH_3$, is elevated in pressure to about 3200 psig through the high pressure plunger pump 46, preheated to about 145°F. in preheater 47 and introduced into the reactor 1 through line 48.

18,383 lbs/hr of gaseous $CO_2$ at about 3200 psig and at about 250°F. is passed through line 56 into reactor 1.

Going back to the first condenser 33, the solution formed in condenser 33 is recirculated through lines 50 and 51 over the packed section 36. The amount of solution formed in condenser 33 and containing 18,170 lbs/hr of ammonium carbamate, 4780 lbs/hr of free ammonia and 8300 lbs/hr of water is passed through line 52, elevated in pressure to about 3200 psig through the high pressure plunger pump 53, passed through line 54 and introduced into reactor 1. The automatic liquid level controller 55 maintains a constant level of solution in condenser 33 by controlling the speed of the reciprocating high pressure plunger pump 53, so that pump 53 continuously delivers to the reactor 1 the carbamate recycle solution in line 54 at exactly the same rate at which it is formed in condenser 33.

The refractometer 57 on line 50 registers the refractive index of the carbamate recycle solution formed in condenser 33.

In this example the ratio of $CO_2$ to water in the carbamate recycle solution at which it is desirable to operate the first condenser 33 is as follows:

18,170 lbs/hr of ammonium carbamate is equivalent to 10,250 lbs/hr of $CO_2$, thus $$\frac{CO_2}{H_2O} = \frac{10,250}{8300} = 1.24$$

If this ratio increases above 1.24 and consequently the crystallization point of the carbamate recycle solution of stream 54 also increases, the proportional increase in refractive index of the solution will be detected by the refractometer 57. This increase in refractive index will be in turn transformed into a proportional signal which will reset one or both control valves 28 and 20 for a larger flow of cooling water through the respective cooling coils 27 and 19. This will result in a drop in temperature and thus in vapor pressure of the solution in condenser 25 and 18, respectively, and in a relative drop in pressure which will be transmitted to the respective decomposers 9 and 14. This temporary drop in pressure in decomposers 9 and 14 will, in turn, cause more water to be evaporated from the aqueous urea solution and more water vapor to be present in the respective overhead lines 11 and 16. By this mechanism more water will be present in streams 24, 32 and ultimately in stream 54.

As soon as the original $CO_2$ to water ratio of about 1.24 is restored, the refractometer will automatically reset the control valves 28 and 20 for the purpose of maintaining the desired and prefixed $CO_2$ to water ratio of about 1.24.

Completely the opposite will happen if the $CO_2$ to $H_2O$ ratio decreases below 1.24, and thus the pressure in decomposers 9 and 14 will be temporarily increased for the purpose of temporarily reducing the amount of water vapor evaporated from the aqueous urea solution in the respective decomposers 9 and 14 and thus of reducing the water vapor content in streams 11 and 16, respectively.

It is obvious that the same ultimate effect can be obtained by varying the pressure in the decomposers 9 and 14 either directly by controlling the valves 59 and 58 on the gaseous streams 11 and 16, respectively, or indirectly by venting more or less gas from the respective condensers 25 and 18 through valves 71 and 72. But in these cases, the urea synthesis process system will be less efficient in comparison to the case wherein the pressure in the decomposers 9 and 14 is indirectly controlled by varying the flow of cooling water through the respective cooling coils 27 and 19.

The level controller and all of the other equipment shown in the FIGURE are all standard components which are well known in the art. It should be clear that various modifications to the present invention would be made within the scope of the invention as set forth in the claims.

A stream containing ammonia, carbon dioxide and water, or a carbon dioxide stream can be added to either one or all of said condensers 18, 25 and 33, from an external source, such as off-gas stream from melamine plant, or other source of ammonia and/or carbon dioxide.

I claim:

1. A system for the synthesis of urea with ammonium carbamate solution recycle, wherein fluid ammonia, fluid carbon dioxide and a solution comprising ammonium carbamate are reacted at elevated pressure and temperature to synthesize urea in a urea reactor, and wherein water balance is maintained in the system, comprising:

sources of fluid ammonia and fluid carbon dioxide;
a source of water:
a urea synthesis reactor having first inlet means coupled to said sources and second inlet means receiving said solution comprising ammonium carbamate, said reactor for reacting said fluid ammonia, fluid carbon dioxide and said solution comprising ammonium carbamate at elevated pressure and temperature therein to produce a urea product stream containing urea, water, unconverted ammonium carbamate and ammonia, said reactor further including outlet means for discharging said urea product stream therefrom;
valve means coupled with said reactor outlet means to reduce the pressure of said urea product stream;
a decomposer equipped with inlet means coupled to the discharge side of said valve means, and including means for removing gases therefrom and means for removing liquid product therefrom, said decomposer including means for heating said product stream at a reduced pressure relative to the pressure in the reactor to decompose unconverted ammonium carbamate to gaseous ammonia and carbon dioxide and to vaporize said ammonia and expel the total mixture of gaseous ammonia and carbon dioxide together with some water vapor from the aqueous urea solution through said gas removing means;
a condenser having at least one inlet means and outlet means, the at least one condenser inlet means being coupled to said gas removing means of the decomposer, said condenser condensing gaseous ammonia and carbon dioxide and water vapor to a liquid phase containing ammonium carbamate, ammonia and water, the liquid phase being fed to the condenser outlet means;
conduit means coupling said outlet means of said condenser to said second inlet means of said reactor for charging recycled ammonium carbamate solution to said reactor;
a refractometer coupled between said condenser outlet means and said second inlet means of said reactor for sensing a refractive index value of said liquid phase recycled to said second inlet of said reactor, said refactive index value being a function of the weight ratio of carbon dioxide as carbamate to water in said liquid phase; and
regulating means including at least one valve means coupled to said water source and controlled by said refractometer for regulating the weight ratio of carbon dioxide to water in said liquid phase in said condenser by varying the flow rate of water to said condenser as a function of deviations of said sensed refractive index value from a reference value which corresponds to a reference weight ratio of carbon dioxide as carbamate to water in said liquid phase to substantially reduce said deviations and maintain said weight ratio substantially at said reference weight ratio.

2. A system according to claim 1 including means coupled to said conduit means between said condenser outlet means and said second inlet of said reactor for increasing the pressure of said recycled liquid phase.

3. A system according to claim 2 wherein said pressure increasing means is coupled to said conduit means between said refractometer and said second inlet of said reactor.

4. A system according to claim 1 wherein said regulating means includes means for varying the temperature in said condenser as a function of said deviations in said sensed refractive index values.

5. A system according to claim 4 wherein said condenser receives a quantity of a cooling fluid, and said temperature varying means comprises means for varying the quantity of cooling fluid to said condenser as a function of said deviations in said sensed refractive index values.

6. A system according to claim 1 wherein said source of water comprises a water supply coupled to said condenser via said valve means of said regulating means.

7. A system according to claim 1 wherein said source of water comprises a water supply coupled to said inlet means of said reactor for said fluid ammonia via said valve means of said regulating means, whereby variation of water flow to said reactor results in variation of the weight ratio of carbon dioxide to water in said liquid phase in said first condenser.

8. A system according to claim 1 wherein said source of water comprises a water supply coupled to said inlet means of said reactor for said fluid carbon dioxide via said valve means of said regulating means, whereby variation of water flow to said reactor results in variation of the weight ratio of carbon dioxide to water in said liquid phase in said first condenser.

9. A system according to claim 1 wherein said source of water comprises a source of water vapor.

10. A system for the synthesis of urea with ammonium carbamate solution recycle, wherein fluid ammonia, fluid carbon dioxide and a solution comprising ammonium carbamate are reacted at elevated pressure and temperature to synthesize urea in a urea reactor, and wherein water balance is maintained in the system, comprising:

sources of fluid ammonia and fluid carbon dioxide;
a urea synthesis reactor having first inlet means coupled to said sources and second inlet means receiving said solution comprising ammonium carbamate, said reactor for reacting said fluid ammonia, fluid carbon dioxide and said solution comprising ammonium carbamate at elevated pressure and temperature therein to produce a urea product stream containing urea, water, unconverted ammonium carbamate and ammonia, said reactor further including outlet means for discharging said urea product stream therefrom;

valve means coupled with said reactor outlet means to reduce the pressure of said urea product stream;

a first decomposer equipped with inlet means coupled to the discharge side of said valve means, and including means for removing gases therefrom and means for removing liquid product therefrom, said first decomposer including means for heating said product stream at a reduced pressure relative to the pressure in the reactor to decompose unconverted ammonium carbamate to gaseous ammonia and carbon dioxide and to vaporize said ammonia and expel the total mixture of gaseous ammonia and carbon dioxide together with some water vapor from the aqueous urea solution through said gas removing means;

a first condenser having at least first and second inlet means and an outlet means, the first inlet means of the first condenser being coupled to said gas removing means of the first decomposer, said first condenser condensing gaseous ammonia and carbon dioxide and water vapor to a liquid phase containing ammonium carbamate, ammonia and water, the liquid phase being fed to the first condenser outlet means;

conduit means coupling said outlet means of said first condenser to said second inlet means of said reactor for charging recycled ammonium carbamate solution to said reactor;

a refractometer coupled between said outlet means of said first condenser and said second inlet means of said reactor for sensing a refractive index value of said liquid phase recycled to said second inlet of said reactor, said refractive index value being a function of the weight ratio of carbon dioxide as carbamate to water in said liquid phase; and at least a second decomposer coupled to receive a liquid product from the first decomposer, said second decomposer including means for removing therefrom and means for removing liquid product therefrom;

at least a second condenser having inlet means and outlet means, the inlet means of said second condenser being coupled to the gas removing means of said second decomposer;

means coupling the outlet means of said second condenser to the second inlet means of the first condenser; and regulating means including at least one valve means controllably coupled to said refractometer for regulating a flow of water to said first condenser to regulate the weight ratio of carbon dioxide to water in said liquid phase in said first condenser as a function of deviations of said sensed refractive index value from a reference value which corresponds to a reference weight ratio of carbon dioxide as carbamate to water in said liquid phase to substantially reduce said deviations and maintain said weight ratio substantially at said reference weight ratio.

11. A system according to claim 10 wherein said regulating means includes valve means coupled to said second decomposer for varying the pressure in said second decomposer as a function of said deviations in said sensed refractive index values, and further comprising means for maintaining the pressure in said second condenser substantially constant, thereby varying the flow rate of water to said first condenser as a function of said deviations of said sensed refractive index value from said reference value.

12. A system according to claim 11 wherein said gas removing means of said second decomposer comprises a conduit means coupled to said second condenser, and said valve means for varying the pressure in said second decomposer includes a variable valve means coupled in said conduit means.

13. A system according to claim 11 comprising means coupled to said second condenser and responsive to the liquid level in said second condenser for varying the flow of liquid product, including water, from said second condenser to said first condenser, the liquid level in said second condenser being varied as a function of the change in pressure in said second decomposer.

14. A system according to claim 10 wherein said regulating means includes valve means coupled to said second condenser for varying the flow of cooling water to said second condenser to thereby vary the temperature in said second condenser as a function of said deviations in sensed refractive index values, thereby varying the flow rate of water to said first condenser as a function of deviations of said sensed refractive index value from said reference value.

15. A system according to claim 14 comprising means coupled to said second condenser and responsive to the liquid level in said second condenser for varying the flow of liquid product, including water, from said second condenser to said first condenser, the liquid level in said second condenser being varied as a function of the change in temperature in said second condenser.

16. A system according to claim 10 wherein said regulating means includes valve means coupled to said second condenser for varying the pressure in said second condenser and in said second decomposer as a function of said deviations in said sensed refractive index values, thereby varying the flow rate of water to said first condenser as a function of deviations of said sensed refractive index value from said reference value.

17. A system according to claim 16 comprising means coupled to said second condenser and responsive to the liquid level in said second condenser for varying the flow of liquid product, including water, from said second condenser to said first condenser, the liquid level in said second condenser being varied as a function of the change in pressures in said second condenser and in said second decomposer.

18. A system according to claim 10 further comprising a source of water, and wherein said regulating means includes valve means coupling said source of water to said second condenser for varying the liquid level therein as a function of said deviations in said sensed refractive index values, thereby varying the flow rate of water to said first condenser as a function of deviations of said sensed refractive index value from said reference value.

19. A system according to claim 18 comprising means coupled to said second condenser and responsive to the liquid level in said second condenser for varying the flow of liquid product, including water, from said second condenser to said first condenser, thereby varying the flow rate of water to said first condenser.

20. A system according to claim 10 wherein said regulating means regulates a flow of water vapor to said first condenser to regulate the weight ratio of carbon dioxide to water in said liquid phase in said first condenser.

* * * * *